United States Patent [19]

Filippini et al.

[11] Patent Number: 4,539,147

[45] Date of Patent: Sep. 3, 1985

[54] PROCESS FOR PREPARING ALPHA-L-ASPARTYL-L-PHENYLALANINE ALKYL ESTERS

[75] Inventors: Andrea Filippini, Prato; Renato Carobbi, Pistoia, both of Italy

[73] Assignee: Sirac SpA, Milan, Italy

[21] Appl. No.: 447,715

[22] Filed: Dec. 7, 1982

[30] Foreign Application Priority Data

Sep. 2, 1982 [IT] Italy ............... 23096 A/82

[51] Int. Cl.³ ........................... C07C 103/52
[52] U.S. Cl. ............................. 260/112.5 R
[58] Field of Search ................. 260/112.5 R

[56] References Cited

U.S. PATENT DOCUMENTS 3,786,039  1/1974  Ariyoshi et al. ............. 260/112.5 R
3,879,372  4/1975  Boesten ....................... 260/112.5 R
3,933,781  1/1976  Bachman et al. ............. 260/112.5 R

OTHER PUBLICATIONS

*Chemical Abstracts*, 78, 554 (1973), Abstract No. 58773f.

Primary Examiner—Delbert R. Phillips
Assistant Examiner—F. T. Moezie
Attorney, Agent, or Firm—Stevens, Davis, Miller & Mosher

[57] ABSTRACT

A process for preparing alpha-L-aspartyl-L-phenylalanine alkyl esters from L-aspartic acid, of which the amino group is protected by bonding it to a 3,5-dimethoxy-α,α-dimethyl-benzyloxycarbonyl group, then transforming this intermediate into the corresponding anhydride by means of a dehydrating agent, then reacting the anhydride with L-phenylalanine alkyl ester, and finally eliminating the protective group by the action of U.V. radiation.

2 Claims, No Drawings

PROCESS FOR PREPARING ALPHA-L-ASPARTYL-L-PHENYLALANINE ALKYL ESTERS

This invention relates to a new process for preparing alpha-L-aspartyl-L-phenylalanine alkyl esters, particularly useful for producing aspartame.

The sweetening action of some α-aspartyl-L-aminoacid esters is well known, their synthesis being described in various documents.

Substantially, such dipeptides are prepared by reacting the L-phenylalanine aminoacid with L-aspartic acid by the following procedures:

(a) condensing the aspartic anhydride protected at the amino group;

(b) condensing the aspartic acid protected at the amino group and esterified at the carboxyl in position β;

(c) directly condensing the aspartic anhydride non-protected at the amino group.

With the first procedure there is always the formation of the two isomers in position α and β. Moreover, if the protective group is the carbobenzyloxy radical, there is a double drawback during synthesis, namely the need to use toxic and dangerous substances, and the need to use final catalytic hydrogenation.

The second procedure enables the required isomer, namely the α, to be obtained alone, but it is long and costly and therefore not convenient industrially.

The third procedure, apparently more simple, is of low importance from the industrial aspect because of its low yields and the difficulty of obtaining the pure α isomer, due to the large-scale formation of byproducts during the synthesis.

The present invention relates to a process for preparing alpha-L-aspartyl-L-phenylalanine alkyl esters of general formula:

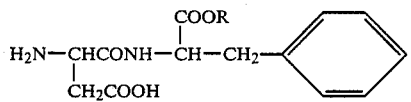

in which R is an alkyl having a small number of C atoms, in particular methyl, characterised in that the amino group of the initial L-aspartic acid is protected by bonding it to the 3,5-dimethoxy-α,α-dimethyl-benzyloxycarbonyl radical.

This intermediate compound with the amino group protected is obtained by reacting L-aspartic acid with 3,5-dimethoxy-α,α-dimethyl-benzyloxycarbonylazide in an acid environment.

This firstly produces the intermediate compound 3,5-dimethoxy-α,α-dimethyl-benzyloxycarbonyl-L-aspartic acid of formula:

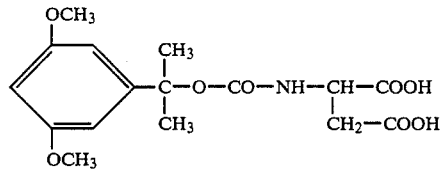

The next stage of the process consists of transforming this intermediate into the corresponding anhydride by the action of a dehydrating agent of the carboxylic acid anhydride or halide type, in particular acetic anhydride.

The anhydride produced in this manner is reacted at ambient temperature in an anhydrous solvent, in particular tetrahydrofuran, with a L-phenylalanine alkyl ester to give the compound of formula:

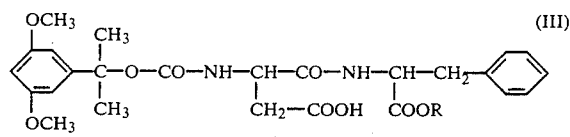

This is an alpha-L-aspartyl-L-phenylalanine alkyl ester in which R is a $C_1$-$C_6$ alkyl, and in which the —$NH_2$ group of the aspartyl radical is protected by the 3,5-dimethoxy-α,α-dimethylbenzyloxycarbonyl radical.

This latter is then eliminated by acting with U.V. rays on said compound in solution, at a temperature of 10°–15° C.

The overall alpha isomer yield is very high.

The use of said protective group is particularly advantageous because it has a considerable photolability in an organic solvent. This enables it to be detached under very mild conditions with a continuous process, so preventing any alteration in the other functional groups of the molecule by degradation.

In practice, the intermediate (III) containing the protective group is passed, in the form of a low concentration solution in an inert organic solvent, particularly tetrahydrofuran, through a quartz tube subjected to U.V. rays originating from a high pressure mercury vapour lamp. The operation is carried out at 10°–15° C., with a flow rate of the order of 1 ml per minute.

The solution of the intermediate (III) obtained in the reaction between the anhydride of the aspartic derivative and the L-phenylalanine alkyl ester can be treated with U.V. rays directly, without separating it from the reaction mixture.

The solution obtained by the U.V. treatment is then concentrated by evaporating the solvent under vacuum, and the dry residue is taken up in a water-ethyl ether mixture.

The unreacted products together with the by-products originating from the degradation of the protective radical go into the ether phase, whereas the final product remains in the aqueous solution, and can be transformed into the corresponding hydrochloride by acidification with HCl, and then obtained in the form of crystals by cooling the solution.

The final product of formula (I) can be obtained from the aqueous hydrochloride solution by adjusting it to pH 4.6 with a $Na_2CO_3$ solution, and crystallizing the product by cooling the aqueous solution.

An embodiment of the invention is described hereinafter by way of non-limiting example, with reference to the preparation of alpha-L-aspartyl-L-phenylalanine methyl ester.

EXAMPLE (a) Synthesis of 3,5-dimethoxy-α,α-dimethyl-benzyloxycarbonyl-L-aspartic acid.

The following substances are fed in the stated order into a flask fitted with a thermometer, mechanical stirrer, dropping funnel and a device for complete distillation:

7.56 g (≃56.8 mM) of L-aspartic acid 49.4 ml (≃113.7 mM) of a 40% w/v solution of trimethylbenzylammonium hydroxide in methanol 50 ml of methanol 10 ml of deionised water.

The mixture is stirred and heated until a clear colorless solution is obtained, the stirring being carried out at 50° C. for 30 minutes.

It is then allowed to cool to 30° C., and the solvent distilled off under reduced pressure. The formation of a white needle-like precipitate having a different appearance than the initial L-aspartic acid is observed. It is evaporated to dryness. The residue obtained is made anhydrous by subjecting it to azeotropic distillation with benzene added in two applications of 125 ml each time, and each time evaporating to dryness.

The actual functionalisation of the amino group is carried out once the trimethylbenzylammonium salt of L-aspartic acid has formed.

100 ml of anhydrous pyridine are added to the anhydrous residue, and stirred for 30 minutes at 40°. A solution of 20 g of 3.5-dimethoxy-α,α-dimethylbenzyloxycarbonylazide in 50 ml of anhydrous pyridine are then added. The reaction mixture is maintained at 40° for 48 hours, after which it is evaporated to dryness under vacuum, and the residue taken up in 125 ml of a 1N sodium hydroxide solution, and transferred into a separating funnel, washing the aqueous phase four times with 100 ml of ethyl ether.

50 g of crushed ice are added to the washed alkaline phase, and acidified to pH 4 with a 50% solution of citric acid in water. About 60 ml are required.

The obtained suspension is poured into a separating funnel, and extracted with 80 ml of methylene chloride four times.

The pink color passes into the organic phase, which is washed twice with 100 ml of water and then dried over anhydrous sodium sulphate.

The organic solution is evaporated under vacuum, and the residue weighed. Yield 87%.

Thin layer chromatography analysis is carried out using silica gel plates (0.2 mm) with a F254 fluorescence indicator.

Mobile phase:

n.butanol-acetic acid-water 11/1/1

(b) sec.butanol-ethyl acetate-water 14/12/5

Detector:

(a) U.V. lamp at 254 nm (b) ninhydrin reagent

Rf table:

| Mobile phase | Detector | DDBC Azide | L-aspartic acid | DDBC L-aspartic acid |
|---|---|---|---|---|
| a | a | 0.91 | — | 0.72 |
|   | b | — | 0.17 | — |
| b | a | 0.94 | — | 0.58 |
|   | b | — | 0.16 | — |

Elementary analysis for $C_{16}H_{21}NO_8$ (355.38): Found: C 54.18; H 6.02; N 3.91. Calculated: C 54.07; H 5.97; N 3.94. M.P. 97°–99° C.

(b) Synthesis of 3,5-dimethoxy-α,α-dimethyl-dibenzyloxy-carbonyl-L-aspartic anhydride 35.5 g of finely divided 3,5-dimethoxy-α,α-dimethylbenzyloxycarbonyl-L-aspartic acid are dissolved under vigorous stirring in 40 ml of acetic anhydride at ambient temperature.

The formation of a white precipitate is observed after 2 hours, and tends to increase with time. A total of about 3 hours are necessary for the reaction to go to completion.

The crystals are filtered under vacuum, washed with a cold solution of anhydrous ethyl ether, and dissolved in a 1:1 mixture of chloroform/ethyl ether under slight heating.

After maintaining the solution for 1 hour at 0°, a crystalline precipitate forms.

The product is filtered off and dried, to give a yield of 78%.

Elementary analysis for $C_{16}H_{19}NO_7$ (337.36): Found: C 56.71; H 5.57; N 4.23. Calculated: C 56.96; H 5.69; N 4.15.

(c) Synthesis of α-L-aspartyl-L-phenylalanine methyl ester

A solution of 1.97 g (11 mM) of L-phenylalanine methyl ester in 20 ml of tetrahydrofuran are added under stirring at ambient temperature to a solution of 3.55 g of 3,5-dimethoxy-α,α-dimethylbenzyloxycarbonyl-L-aspartic anhydride (10 mM) in 20 ml of tetrahydrofuran.

After leaving the mixture stirring overnight, it is diluted about 10 times with the same solvent and exposed to ultraviolet radiation at a temperature of about 13° C., with a flow rate of 1 ml/minute.

Having detached the protector group in this manner, the solution is evaporated to dryness under vacuum. The residue is taken up and shaken in 80 ml of a 1:1 water/ethyl ether mixture. Any unreacted L-phenylalanine methyl ester together with the products deriving from the demolition of the protective group pass into the organic phase.

A small sample of the aqueous phase containing α and β aspartame is analysed for these latter using an Amino Acid Autoanalyser 3A29, under the analysis conditions stated hereinafter. The yield as the sum of the two isomers is 85%, there being 80% α and 20% β isomer present than α isomer.

The aqueous phase is cooled to 5% and acidified with concentrated hydrochloric acid. The mixture is stirred vigorously until slight opalescence forms, after which it is left overnight in a refrigerator.

The needle-like crystals of the formed α-L-aspartyl-L-phenylalanine methyl ester hydrochloride dihydrate are separated from the solution by filtration under vacuum.

The product obtained is dissolved in about 50 ml of water, its pH is adjusted to 2.7-3 with 10% $Na_2CO_3$, and is heated until a clear solution is obtained (T about 55° C.).

White crystals form almost immediately.

After leaving overnight at 5° C., the α-L-aspartyl-L-phenylalanine methyl ester hemihydrate which forms is filtered off and dried to give an overall yield of 64% of pure product.

Thin layer chromatography analysis: Silica gel plate (0.2 mm). Mobile phase: n.butanol-acetic acid-water 60/20/20. Detector: ninhydrin reagent. Rf: isomer α 0.65, isomer β 0.57.

Chromatography analysis with Amino Acid Autoanalyser model 3A29 of Carlo Erba: Column: stainless steel 25×0.46 cm. Stationary phase: strongly cationic resin of Na form Carlo Erba mod. 3AR/6/DC/20.

Mobile phase: sodium citrate buffers pH 3.30, 20 minutes; pH 3.60, 20 minutes; pH 4.07, 50 minutes.

Column temperature: 64° C. Total flow rate: 0.8 ml/minute (0.5 ml/minute buffer). Pressure: 40-50 atmospheres. AUFS: 0.5. Retention times: isomer α about 74 minutes, isomer β about 47 minutes.

Elementary analysis for $C_{14}H_{18}N_2O_5$ (294.30): Found: C 57.57; H 6.01; N 9.57. Calculated: C 57.14; H 6.16; N 9.52. M.P. 245°-247° C.

We claim:

1. A process for preparing alpha-L-aspartyl-L-phenylalanine alkyl esters of formula:

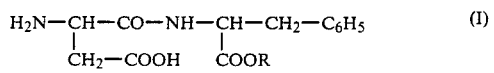
(I)

in which R is $C_1$–$C_6$ alkyl wherein
(a) aspartic acid is reacted with 3,5-dimethoxy-α,α-dimethyl-benzyloxycarbonyl-azide in an anhydrous environment;
(b) the resultant 3,5-dimethoxy-α,α-dimethyl-benzyloxy-carbonyl aspartic acid is reacted with acetic anhydride in excess to give the corresponding anhydride;
(c) the protected aspartic anhydride is reacted with the L-phenylalanine alkyl ester in tetrahydrofuran solvent at ambient temperature; and
(d) the resultant compound of formula:

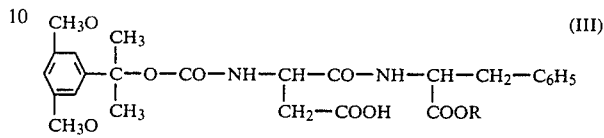
(III)

is subjected to an operation in which the protective group is split by the action of U.V. radiation on a solution of the product in tetrahydrofuran solvent at 10°-15° C.

2. A process as claimed in claim 1, in which α-L-aspartyl-L-phenylalanine methyl ester is prepared.

* * * * *